United States Patent [19]

Raymond

[11] Patent Number: 5,554,497
[45] Date of Patent: Sep. 10, 1996

[54] CARDIOPLEGIC SOLUTION FOR ARRESTING AN ORGAN

[75] Inventor: Richard M. Raymond, Charlotte, N.C.

[73] Assignee: Charlotte-Mecklenburg Hospital Authority, Charlotte, N.C.

[21] Appl. No.: 354,503

[22] Filed: Dec. 12, 1994

[51] Int. Cl.$^6$ .................................................. A01N 1/02
[52] U.S. Cl. .................................... 435/1.2; 435/1.1
[58] Field of Search ................................ 435/1, 283

[56] References Cited

U.S. PATENT DOCUMENTS

| | | | |
|---|---|---|---|
| 4,798,824 | 1/1989 | Belzer et al. | 514/60 |
| 4,873,230 | 10/1989 | Belzer et al. | 514/60 |
| 4,879,283 | 11/1989 | Belzer et al. | 514/60 |
| 4,920,044 | 4/1990 | Bretan, Jr. | 435/1 |
| 5,145,771 | 9/1992 | Lemasters et al. | 435/1 |

FOREIGN PATENT DOCUMENTS 2089336  8/1993  Canada.

OTHER PUBLICATIONS

Dennis S., Effects of Proton Buffering . . . Circulation Research 66(4) 1990, pp. 1156–1159.

Galinanes M., Long–Term Hypothermic Storage . . . J of Heart & Lung Transpian 11(4) PT 1 1992, pp. 624–635.

Moffat M., Protective Effects of the Potent Na/H . . . J Mol Cell Cardiol(25) 1993 pp. 959–971.

Pierce G. Modulation of Cardiac Performance . . . J of Pharm Exp Thera 265 (3) 1993 pp. 1280–1291.

Manuel Galinanes, MD, Toshifumi Murashita, MD, and David J. Hearse, PhD, FACC, DSc, Long–Term Hypothermic Storage of the Mammalian Heart for Transplantation: A Comparison of Three Cardioplegic Solutions, *The Journal of Heart and Lung Transplantation*, vol. II, No. 4, Part 1, Jul./Aug. 1992, pp. 624–635.

Steven C. Dennis, William A. Coetzee, Edward J. Cragoe, Jr., and Lionel H. Opie, Effects of Proton Buffering and of Amiloride Derivatives of Reperfusion Arrhythmias in Isolated Rat Hearts, *Circulation Research*, vol. 66, No. 4, Apr. 1990, pp. 1156–1159.

Pankaj Mankad, FRCS(C/Th), Zdenek Slavik, MD, and Magdi Yacoub, FRCS, Endothelial dysfunction caused by University of Wisconsin preservation solution in the rat heart, *The Journal of Thoracic and Cardiovascular Surgery*, vol. 104, No. 6, Dec. 1992, pp. 1618–1624.

Martin M. Pike, Cameron Su Luo, M. Daniel Clark, Katharine A. Kirk, Masafumi Kitakaze, Michael C. Madden, Edward J. Cragoe, Jr., and Gerald M. Pohost, NMR measurement of Na+ and cellular energy in ischemic rat heart: role of Na+–H+ exchange, *The American Physiological Society*, 0363–6135/93, pp. H2017–H2026.

Margaret P. Moffat and Morris Karmazyn, Protective Effects of the Potent Na/H Exchange Inhibitor Methylisobutyl Amiloride Against Post–ischemic Contractile Dysfunction in Rat and Guinea–pig Hearts, *J. Molec. Cell Cardiol.*, (25), 1993, pp. 959–971.

Ganghong Tian, MD, MSc, Karen E. Smith, MSc, George P. Biro, MD, PhD, Keith W. Butler, PhD, Nick Haas, BSc, Jack Scott, BSc, Russell Anderson, MD, PhD, and Roxanne Deslauriers, PhD, A Comparison of UW Cold Storage Solution and St. Thomas' Solution II: A$^{31}$P NMR and Functional Study of Isolated Porcine Hearts, *The Journal of Heart and Lung Transplantation*, vol 10, No. 6, Nov./Dec. 1991, pp. 975–985.

Grant N. Pierce, William C. Cole, Kanzhi Liu, Jamid Massaeli, Thane G. Maddaford, Yi Jing Chen, Caroline D. McPherson, Shilpa Jain and David Sontag, Modulation of Cardiac Performance by Amiloride and Several Selected Derivatives of Amiloride, *The Journal of Pharmacology and Experimental Therapeutics*, vol. 265, No. 3, 1993, pp. 1280–1291.

*Primary Examiner*—Ralph J. Gitomer
*Attorney, Agent, or Firm*—Bell, Seltzer, Park & Gibson, P.A.

[57] ABSTRACT

There is provided cardioplegic solutions for arresting an organ intended for transplantation and preservation solutions for perfusing and storing an organ while awaiting transplantation. The cardioplegic solutions include, per liter of solution, a balanced isotonic solution of sodium, potassium, calcium, and magnesium ions and bicarbonate in a physiologically acceptable amount, from about 0.5 μM to about 2.0 μM of an amiloride-containing compound; and water sufficient to make a liter of solution. The amiloride-containing compound may be amiloride, hexamethylene amiloride, dimethyl amiloride, ethyl isopropyl amiloride or methyl isobutyl amiloride. The preserving solutions are based on the isotonic solutions described and include other components such as EDTA, a small amount of adenosine, and at least one antioxidant. There is also provided a method for arresting an organ, storing an organ and transplanting an organ all at room temperature for up to at least 24 hours.

28 Claims, No Drawings

CARDIOPLEGIC SOLUTION FOR ARRESTING AN ORGAN

BACKGROUND OF THE INVENTION

1. Field of the Invention

The present invention relates to cardioplegic solutions, to preservation solutions, and to methods for transplanting organs. More particularly, this invention relates to cardioplegic solutions for arresting an organ for transplantation, to preservation solutions for perfusing and storing an organ while awaiting implantation, and to methods for using the cardioplegic and preserving solutions during transplantation of an organ.

2. The Prior Art

A great deal of research progress has been made over the years in understanding cellular mechanisms, as well as developing new transplantation techniques for keeping organs viable not only during storage but also after reperfusion of these organs. As a result, organ transplantation, including heart transplantation, is an established elective operation. A significant factor limiting the clinical application of organ transplantation is the deviation of viability of the organ after removal from the donor.

At present, the two most frequently used methods for heart transplantation are simple hypothermic storage and continuous pulsatile perfusion. With simple hypothermic storage, the heart is arrested with a cardioplegic solution, then removed from the donor and cooled rapidly. This is usually achieved by a combination of cooling and a short period of perfusion to drop the heart temperature as quickly as possible to a temperature between 0° C. and 4° C. where it may be held up to about 6 hours. While cold storage enables organs to be transplanted, the time during which the organ is viable is short. Cold storage decreases the rate at which intracellular enzymes, essential cellular components necessary for organ viability, degrade but does not stop metabolism.

The second method of organ preservation which has undergone extensive investigation, continuous pulsatile perfusion, includes the following steps: (1) pulsatile flow, (2) hypothermia, (3) membrane oxygenation, and (4) a perfusate containing both albumin and lipids. Although being more technically complex and costly, the advantages to using continuous pulsatile perfusion over simple hypothermia include longer viability of the organ and viability testing prior to implantation.

The compositions of numerous cardioplegic and preservation solutions have been extensively studied. For example, the protective properties of three cardioplegic solutions were compared by Galinanes et al. (M. Galiñanes, T. Murashita and D. J. Hearse (1991) *The Journal of Heart and Lung Transplantation* (11) 624–635, at low temperatures and short time periods. A comparison of cold preservation solutions was set forth in G. Tian et al. (1991) *The Journal of Heart and Lung Transplantation* (10) 975–985, where the cold preservation solutions limited the storage time of the organs.

A storage solution for preserving organs which can be used at temperatures from 0° C. to 37° C. but was limited in storage time was disclosed in U.S. Pat. No. 5,145,771 to Lemasters et al. The solution requires the use of the colloid, hydroxyethyl starch, for oncotic support against interstitial edema. In the present invention edema is not a problem because no oxygen-derived free radicals are available to injure the organ.

Preserving organs at between 0° C. and 4° C. results in damage to the organ during storage and upon reperfusion with a warm reperfusion solution. Injury to the organ occurs through the loss of endothelial cells due to dissolved oxygen in the reperfusion solution. Although some of the solutions of the prior art have been useful to extend the storage time of donor organs and lessen injury to the organ upon reperfusion, cell injury still occurs. Therefore, it is desirable to extend the viable organ life and improve the quality of the transplanted organ. Extending the organ viability allows sufficient time for compatibility testing of the donor and recipient and increased organ availability.

The recovery of cardiac function is also greatly influenced by the time lapse between removal from the donor and reperfusion as well as the efficacy of protective interventions used during that period. To overcome the deleterious effects of ischemia, techniques such as intermittent or continuous perfusion have been used. Finally, reperfusion itself, although necessary for the survival of the tissue, may initiate a series of events known as reperfusion induced injury, which, if occurring, limit the extent or rate of recovery. Thus, modification of the nature of reperfusion is desirable to improve the recovery of the ischemic/reperfused myocardium.

More particularly, as a result of the deprivation of circulation, and thus oxygen (i.e., ischemia) during transplantation, the sodium pump, which normally maintains the intracellular composition high in potassium, magnesium, and phosphate and low in sodium and chloride, ceases to function due to the lack of energy, resulting in an inflow of sodium and chloride into the cells, and an outflow of potassium and to a lesser extent magnesium from the cells. The result of these rapid changes in $Na^+$—$H^+$ distribution in the cell is a net gain, not merely an exchange, of intracellular ions followed by water and a profound loss of potassium and magnesium resulting in damage to the organ. The protective effects of Na/H exchange inhibitors, including amiloride and its analogs in the reperfused myocardium has been studied by Moffat, et al. (M. P. Moffat and M. Karmazyn, (1993), *J. Molec. Cell Cardiol* (25), 959–971).

It is therefore the general object of the present invention to provide cardioplegic solutions for arresting organs intended for transplantation and preserving solutions for pulsating and storing organs while awaiting implantation each of which inhibits ion exchange, extends the vitality of the organ, and reduces damage to the cells.

Another object of the present invention is to provide a method for arresting and preserving organs which extend the maximum life of the organ during transplantation.

Yet another object of the present invention is to provide a method of transplanting organs in which storage of the organ may be carried out at room temperature for up to at least 24 hours without significant damage to the organ.

Other objects, features, and advantages of the invention will be apparent from the following details of the invention as more fully described.

SUMMARY OF THE INVENTION

In accordance with these objects and the principles of this invention, there are disclosed cardioplegic solutions and preserving solutions for use in the transplantation of organs, and to methods for transplanting organs using the solutions, which methods increase storage times and lessen injury to the organ.

It has been found that a cardioplegic solution containing an amiloride-containing compound is effective in achieving the objectives of this invention. In one aspect of this invention, the cardioplegic solution includes a balanced isotonic solution including sodium, potassium, calcium and magnesium ions and bicarbonate in a physiologically acceptable amount, from about 0.5 µM to about 2.0 µM amiloride-containing compound, and water sufficient to make a liter of solution.

The inclusion in the isotonic solution of an amiloride-containing compound may be amiloride itself, or amiloride analogs, such as hexamethylene amiloride (HMA), dimethyl amiloride (DMA), ethyl isopropyl amiloride (EIPA), or methyl isobutyl amiloride (MIA), all of which inhibit the $Na^+$—$H^+$ exchange in the organ cells. Dimethyl amiloride is particularly preferred.

The cardioplegic solution also preferably contains glucose to enhance organ preservation, adenosine to prevent fibrillation of the organ prior to removal from the donor, and EDTA as a chelating agent. Optionally, the cardioplegic solution contains heparin and at least one antioxidant.

The preservation solution, while similar to the cardioplegic solution in starting composition in that it is based on a balanced isotonic solution including sodium, potassium, calcium, magnesium ions and bicarbonate in a physiologically acceptable amount differs in significant respects. For example, the preservation solution includes less potassium chloride than the cardioplegic solution and no amiloride. In addition, since the organ has been arrested by the cardioplegic solution, when the preservation solution includes much less adenosine and heparin is not normally needed.

The preservation solution preferably includes at least one antioxidant, such as, dimethyl thiourea (DMTU), catalase as a hydrogen peroxide scavenger and apoferritin to decrease iron content within the preservation solution. In addition, the preservation solutions optionally may include hormones, such as insulin and prostaglandin and antibiotics.

The invention also provides a method for transplanting an organ which includes steps for arresting and removing the organ from the donor, and for preserving and storing the organ intended for implantation. The method of the invention includes arresting the organ to be donated with the cardioplegic solution. The organ is removed and connected to a perfusion apparatus where it is maintained at a temperature between about 0° C. to about 37° C., preferably from about 15° C. to about 25° C. while perfusing with the preservation solution. Thus, the novel features of the present invention include storing the organ at warm temperatures, i.e., up to about room temperature, while perfusing the organ. It is believed that the ability to store the organ at or near room temperature prevents mechanical damage that can result from cold storage, and that continuous perfusion with the preservation solution maintains the organ's metabolic requirements and avoids potential metabolic blocks. As a result, storage times for the organ can be increased up to at least 24 hours.

DETAILED DESCRIPTION OF THE INVENTION

The present invention is directed to new cardioplegic solutions for an arresting organ intended for transplantation and to new preservation solutions for storing and perfusing organs intended for implantation in a patient requiring such implant. Suitable organs on which the solutions of this invention may be used include, for example, heart, liver, kidney and pancreas.

The individual components of the present invention are all nontoxic and have been found to be stable during storage. While some of the components of the present invention are similar to those of other known cardioplegic solutions, it has surprisingly been found that the addition of amiloride or an amiloride-containing compound to a balanced isotonic solution including sodium, potassium, calcium, magnesium, and bicarbonate ions in a physiologically acceptable amount to form a cardioplegic solution and its use in combination with the preservation solutions of the present invention allows organs to be preserved at room temperature for at least 24 hours without significant damage to the organ.

Both the cardioplegic solutions and the preservation solutions of the present invention are based on a balanced isotonic solution including sodium, potassium, calcium and magnesium ions as well as glucose and sodium bicarbonate in a physiologically acceptable amount. Certain of these types of solutions are well known, such as the one described below, known as Krebs-Henseleit-bicarbonate solution, which has the following composition:

TABLE 1

| Concentration Ranges in 1 Liter | |
| --- | --- |
| NaCl | 85 mM to 145 mM |
| KCl | 3 mM to 30 mM |
| $CaCl_2$ | 0.5 mM to 2.5 mM |
| $KH_2PO_4$ | 0.7 mM to 1.3 mM |
| $MgSO_4$ | 0.9 mM to 4.8 mM |
| $NaHCO_3$ | 15 mM to 35 mM |
| Glucose | 1.0 mM to 50 mM |

The Cardioplegic Solution

The cardioplegic solution is made by starting with the balanced isotonic solution described above. The amount of potassium chloride in the cardioplegic solution is preferably from about 20 mM to about 30 mM. To the balanced isotonic solution is added an amiloride-containing compound in an amount from about 0.5 µM to about 2.0 µM, preferably 1.0 µM. By amiloride-containing compound, it is meant to include amiloride and amiloride analogs. The addition of amiloride, designated chemically as 3,5-diamino-6-chlor-N-(diaminomethylene) pyrazinecarboxamide monohydrochloride has been found to inhibit the $Na^+$—$H^+$ exchange. Other amiloride-containing compounds or analogues which may be used in the cardioplegic solution include, for example, hexamethylene amiloride (HMA) designated chemically as 5-(N,N-hexamethylene)amiloride, dimethyl amiloride (DMA) designated 5-(N,N-dimethyl)-amiloride, ethyl isopropyl amiloride (EIPA), designated 5-(N-ethyl-N-isopropyl)-amiloride, and methyl isobutyl amiloride (MIA), designated 5-(N-methyl-N-isobutyl)-amiloride. (Merck Sharpe & Dohme, West Point, Pa.).

To be effective, the cardioplegic solution needs to prevent fibrillation of the organ in a relatively short period of time, e.g., 2 minutes to 5 minutes or less. For that purpose, adenosine is added to the solution in an amount from about 5 µM to about 15 µM per liter, preferably about 10 µM per liter. Adenosine rapidly arrests the heart (within seconds), improves the preservation properties and increases the glucose uptake.

The cardioplegic solution also preferably includes ethylene diaminetetraacetic acid (EDTA) in an amount from 0.5 mM to about 1.5 mM as a chelating agent. The solution also may optionally contain other ingredients, such as at least one antioxidant, for example, catalase, in an amount effective to inhibit the generation of oxygen-derived free radicals via hydrogen peroxide.

Heparin is used in carrying out the method of this invention, and may be included either directly in the cardioplegic solution or it may be administered to the donor organ separately. The addition of heparin in an amount of from about 500 units to about 1500 units, preferably 1000 units is required to prevent blood clots from forming within the coronary arteries during cardioplegic arrest and excision prior to organ storage and implantation.

The Preservation Solution

The preservation solution is designed to prevent various mechanisms which cause injury to the organ and thus must be a composition that (1) prevents or restricts intracellular acidosis, (2) prevents the expansion of intracellular space, (3) prevents injury from oxygen-derived free radicals, especially during reperfusion, (4) enables the regeneration of high-energy phosphate compounds during reperfusion, and (5) sustains appropriate metabolic requirement.

While the cardioplegic solution and the preservation solution begin with the balanced isotonic solution described above there are significant differences in the final compositions. For example, the preservation solution begins with the isotonic solution, wherein the potassium concentration is maintained at preferably from 3 mM to about 8 mM. Magnesium chloride may be used in place of potassium chloride.

While adenosine is included in the preservation solution, the amount of adenosine is considerably less than the amount of adenosine present in the cardioplegic solution because the organ has been previously arrested. The amount of adenosine in the preservation solution is normally from 0.7 µM to about 2.0 µM, preferably about 1.0 µM.

The cardioplegic solution also preferably includes ethylene diaminetetraacetic acid (EDTA) in an amount from 0.5 mM to about 1.5 mM as a chelating agent. It has also been found desirable to add from 10 nM to about 100 nM of caprylic acid which helps the solution to bypass blocked fatty acid utilization and from 10 µg/L to 100 µg/L of apoferritin which serves to eliminate iron (Fe++) which causes breakdown of the cells.

Suitable antioxidants include, but are not limited to, allopurinol, desferrioxamine, glutathione, beta-carotene, catalase, superoxide dismutase, dimethyl thiourea (DMTU), dichloroacetic acid, diphenyl phenylene diamine (DPPD), mannitol or cyanidanol in an amount effective to inhibit the generation of oxygen-derived free radicals. The antioxidants are present in an amount from 1 nM to 10 nM.

Optional components ingredients include, for example, hormones, such as insulin and prostaglandin and antibiotics.

Method of Use

The transplantation method of the present invention is to arrest the organ using the cardioplegic solution, preserve and store the organ with the preservation solution and reperfuse with the preservation solution.

In a preferred method, sufficient cardioplegic solution is injected to arrest, for example the heart and prevent fibrillation. The surgeon then removes the organ and connects the heart to a perfusion apparatus comprising tubing and pumps. The preservation solution is then perfused through the heart while gassed with oxygen and carbon dioxide while it is awaiting implantation into a patient. The method of perfusing the heart can be at either a constant flow or pressure.

The solution can be used at all temperatures ranging from 0° C. to normal body temperature, 37° C. At temperatures of from about 12° C. to about 37° C., the solution is more protective than other known preservation solutions. Unlike other storage solutions, it continues to be protective above 10° C. for at least 24 hours.

The following examples are provided to further illustrate the present invention and are not to be construed as limiting the invention in any manner.

EXAMPLE 1

A liter of cardioplegic solution having the following composition was prepared.

| | |
|---|---|
| NaCl | 118 mM |
| KCl | 30 mM |
| $CaCl_2$ | 1.75 mM |
| $KH_2PO_4$ | 1.2 mM |
| $MgSO_4$ | 1.2 mM |
| $NaHCO_3$ | 25 mM |
| Glucose | 11 mM |
| Adenosine | 10 µM |
| EDTA | 1.0 mM |
| DMA | 1.0 µM |
| Heparin | 1000 units |
| Distilled, deionized water | q.s. |

Into a 1000 mL volumetric flask the Krebs-Henseleit solution was added and double distilled water was added to make one liter while stirring. The rest of the components were added one at a time. After all the components were added the pH was adjusted to 7.3 with NaOH and the flask was gassed with $O_2/CO_2$:95/5%. The solution was stirred for about thirty minutes and filtered to remove any undissolved particles (5.0µ porosity filter). After sterile filtration the solution was ready to use.

EXAMPLE 2

A liter of preservation solution having the following composition was prepared.

| | |
|---|---|
| NaCl | 118 mM |
| KCl | 4.7 mM |
| $CaCl_2$ | 1.75 mM |
| $KH_2PO_4$ | 1.2 mM |
| $MgSO_4$ | 1.2 mM |
| $NaHCO_3$ | 25 mM |
| Glucose | 11 mM |
| Adenosine | 1.0 µM |
| EDTA | 1.0 mM |
| Apoferritin | 100 µg/L |
| Catalase | 10 µg/L |
| DMTU | 10 nM |
| DPPD | 10 nM |
| Caprylic Acid | 50 nM |
| Distilled, deionized water | q.s. |

The preservation solution was prepared in much the same manner as the cardioplegic solution of Example I, that is, by adding a Krebs-Heneseleit solution to a 1000 mL volumetric flask with double distilled water to make one liter while stirring. The rest of the components were added one at a time and the pH of the solution was adjusted to about 7.3 with NaOH and gassed with 95% oxygen plus 5% carbon dioxide. The solution was stirred for about thirty minutes and filtered to remove any undissolved particles (5.0μ porosity filter). After sterile filtration the solution was ready to use.

EXAMPLE 3

A female mongrel dog weighing about 20 kg. was anesthetized. An IV hydrating solution of 5.0% dextrose in 0.45% saline at 75 cc/hr was given throughout the procedure. The heart was exposed by a sternotomy. The cardioplegic solution of Example 1 was administered to arrest the heart, the heart was then excised. The heart was placed in ice and promptly transferred to the laboratory and placed in a perfusion apparatus at room temperature where the aorta was attached to a tube for continuous perfusion with the preserving solution of Example 2. After 2–3 minutes the heart started beating at a pulse rate of 50 beats per minute. Excess preserving solution was allowed to fill the container until the heart was covered to provide buoyancy for the heart so as not to injure the aorta. Perfusion with the solution from Example 2 continued throughout the storage time. The heart continued to beat for over 24 hours.

This experiment demonstrates that the cardioplegic and preservation solutions and methods of the present invention increase the preservation time between harvesting an organ and transplantation and allows the organ to remain at room temperature without serious degradation of the organ cells.

The present invention has been described in detail and with particular reference to the preferred embodiments. Those skilled in the art will appreciate that changes can be made without departing from the spirit and scope thereof. Accordingly, the present invention is to be defined by the following claims, with equivalents of the claims to be included therein.

What is claimed is:

1. A cardioplegic solution for arresting a heart intended for transplantation comprising, per liter of solution:
   (a) a balanced isotonic solution comprising sodium, potassium, calcium, magnesium and bicarbonate ions in a physiologically acceptable amount;
   (b) from about 0.5 μM to about 2.0 μM of an amiloride-containing compound; and
   (c) water.

2. The cardioplegic solution according to claim 1, wherein said amiloride-containing compound is a compound selected from the group consisting of amiloride, hexamethylene amiloride, dimethyl amiloride, ethyl isopropyl amiloride and methyl isobutyl amiloride.

3. The cardioplegic solution according to claim 1, wherein said amiloride-containing compound is dimethyl amiloride.

4. The cardioplegic solution according to claim 1, further comprising from about 0.5 mM to about 1.5 mM of EDTA.

5. The cardioplegic solution according to claim 1, further comprising from about 5.0 μM to about 15 μM of adenosine.

6. The cardioptegic solution according to claim 1, further comprising from about 500 units to about 1500 units of heparin.

7. The cardioplegic solution according to claim 1, further comprising an antioxidant in an amount effective to inhibit the generation of oxygen-derived free radicals.

8. A cardioplegic solution for arresting a heart intended for transplantation comprising, per liter of solution:

| | |
|---|---|
| NaCl | 85 mM to 145 mM |
| KCl | 20 mM to 30 mM |
| CaCl$_2$ | 0.5 mM to 2.5 mM |
| KH$_2$PO$_4$ | 0.7 mM to 1.3 mM |
| MgSO$_4$ | 0.9 mM to 4.8 mM |
| NaHCO$_3$ | 15 mM to 35 mM |
| Glucose | 1.0 mM to 50 mM |
| EDTA | 0.5 mM to 1.5 mm |
| Distilled, deionized water | q.s. | and from about 0.5 μM to about 2.0 μM of an amiloride-containing compound.

9. The cardioplegic solution according to claim 8, wherein said amiloride-containing compound is a compound selected from the group consisting of amiloride, hexamethylene amiloride, dimethyl amiloride, ethyl isopropyl amiloride and methyl isobutyl amiloride.

10. The cardioplegic solution according to claim 8, wherein said amiloride containing compound is dimethyl amiloride.

11. The cardioplegic solution according to claim 8, further comprising from about 5.0 μM to about 15 μM of adenosine.

12. The cardioplegic solution according to claim 8, further comprising from about 500 units to about 1500 units of heparin.

13. The cardioplegic solution according to claim 8, further comprising an antioxidant in an amount effective to inhibit the generation of oxygen-derived free radicals.

14. A cardioplegic solution for arresting a heart intended for transplantation comprising, per liter of solution:

| | |
|---|---|
| NaCl | 118 mM |
| KCl | 30 mM |
| CaCl$_2$ | 1.75 mM |
| KH$_2$PO$_4$ | 1.2 mM |
| MgSO$_4$ | 1.2 mM |
| NaHCO$_3$ | 25 mM |
| Glucose | 11 mM |
| Adenosine | 10 μM |
| EDTA | 1.0 mM |
| Dimethyl amiloride | 1.0 μM |
| Heparin | 1000 units |
| Distilled, deionized water | q.s. |

15. A method for removing a heart from a mammal intended for implantation in a mammal requiring such implantation, said method comprising:
   arresting said heart prior to removal from a donor with a solution comprising, per liter of solution:
   (a) a balanced isotonic solution comprising sodium, potassium, calcium, magnesium, and bicarbonate ions in a physiologically acceptable amount;
   (b) from about 0.5 μM to about 2.0 μM of an amiloride-containing compound; and
   (c) water.

16. The method according to claim 15, in which said amiloride-containing compound is a compound selected from the group consisting of amiloride, hexamethylene amiloride, dimethyl amiloride, ethyl isopropyl amiloride and methyl isobutyl amiloride.

17. The method according to claim 15, in which said amiloride-containing compound is dimethyl amiloride.

18. The method according to claim 15, in which said solution further comprises from about 0.5 mM to about 1.5 mM EDTA.

19. The method according to claim 15, in which said solution further comprising from about 5.0 μM to about 15 μM of adenosine.

20. The method according to claim 15, in which said solution further comprising from about 500 units to about 1500 units of heparin.

21. The method according to claim 15, in which said solution further comprising at least one antioxidant in an amount effective to inhibit the generation of oxygen-derived free radicals.

22. A method for removing the heart from a mammal intended for transplantation, said method comprising:

arresting the heart prior to removal from a donor with a solution comprising, per liter of solution:

| | |
|---|---|
| NaCl | 85 mM to 145 mM |
| KCl | 3 mM to 30 mM |
| $CaCl_2$ | 0.5 mM to 2.5 mM |
| $KH_2PO_4$ | 0.7 mM to 1.3 mM |
| $MgSO_4$ | 0.9 mM to 4.8 mM |
| $NaHCO_3$ | 15 mM to 35 mM |
| Glucose | 1.0 mM to 50 mM |
| EDTA | 0.5 mM to 1.5 mm |
| Distilled, deionized water | q.s. | and from about 0.5 μM to about 2.0 μM of an amiloride-containing compound.

23. The method according to claim 22, wherein said amiloride-containing compound is a compound selected from the group consisting of amiloride, hexamethylene amiloride, dimethyl amiloride, ethyl isopropyl amiloride and methyl isobutyl amiloride.

24. The method according to claim 22, wherein said amiloride-containing compound is dimethyl amiloride.

25. The method according to claim 22, in which said solution further comprising from about 5 μM to about 15 μM of adenosine.

26. The method according to claim 22, in which said solution further comprising from about 500 units to about 1500 units of heparin.

27. The method according to claim 22, in which said solution further comprising at least one antioxidant in an amount effective to inhibit the generation of oxygen-derived free radicals.

28. A method for removing a heart from a mammal intended for implantation, said method comprising:

arresting the heart prior to removal from a donor with a solution comprising, per liter of solution:

| | |
|---|---|
| NaCl | 118 mM |
| KCl | 30 mM |
| $CaCl_2$ | 1.75 mM |
| $KH_2PO_4$ | 1.2 mM |
| $MgSO_4$ | 1.2 mM |
| $NaHCO_3$ | 25 mM |
| Glucose | 11 mM |
| Adenosine | 10 μM |
| EDTA | 1.0 mM |
| Dimethyl amiloride | 1.0 μM |
| Heparin | 1000 units |
| Distilled, deionized water | q.s. |

* * * * *

UNITED STATES PATENT AND TRADEMARK OFFICE
CERTIFICATE OF CORRECTION

PATENT NO. : 5,554,497

DATED : September 10, 1996

INVENTOR(S) : Richard M. Raymond

It is certified that error appears in the above-identified patent and that said Letters Patent is hereby corrected as shown below:

On the cover page, Publication References, Column 1, line 4, delete "Transpian" and insert --Transplan.-- therefor.

On the cover page, Publication References, Column 1, line 13, delete "II" and insert --11-- therefor.

On the cover page, Publication References, Column 1, line 17, delete "of" and insert --on-- therefor.

On the cover page, Publication References, Column 2, lines 3-4, delete "measurement" and insert --measurements-- therefor.

On the cover page, Publication References, Column 2, line 4, delete "Na+" and insert --$Na^+$-- therefor.

On the cover page, Publication References, Column 2, line 5, delete "Na+-H+" and insert --$Na^+$-$H^+$-- therefor.

On the cover page, Publication References, Column 2, line 20 delete "Jamid" and insert --Hamid-- therefor.

Column 1, line 53, delete "Galianes" and insert --Galiañes-- therefor (both occurrences).

Column 1, line 54, delete "(1991)" and insert --(1992)-- therefor.

Column 2, line 21, after "recovery" delete the comma (,) and insert a period (.).

UNITED STATES PATENT AND TRADEMARK OFFICE
CERTIFICATE OF CORRECTION

PATENT NO. : 5,554,497

DATED : September 10, 1996

INVENTOR(S) : Richard M. Raymond

It is certified that error appears in the above-identified patent and that said Letters Patent is hereby corrected as shown below:

Column 5, line 54, delete "components" and insert --component-- therefor.

Column 7, line 53, delete "cardioptegic" and insert --cardioplegic-- therefor.

Column 8, line 14, delete "amiloride containing" and insert --amiloride-containing-- therefor.

Column 9, line 13, (next to last line of 2nd Col.) delete "mm" and insert --mM-- therefor.

Signed and Sealed this

Sixteenth Day of September, 1997

*Attest:*

BRUCE LEHMAN

*Attesting Officer*   Commissioner of Patents and Trademarks